United States Patent
Koehler et al.

(10) Patent No.: US 10,945,691 B2
(45) Date of Patent: Mar. 16, 2021

(54) SENSITIVITY OPTIMIZED PATIENT POSITIONING SYSTEM FOR DARK-FIELD X-RAY IMAGING

(71) Applicant: KONINKLIJKE PHILIPS N.V., Eindhoven (NL)

(72) Inventors: Thomas Koehler, Norderstedt (DE); Andriy Yaroshenko, Garching (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/497,066

(22) PCT Filed: Feb. 27, 2018

(86) PCT No.: PCT/EP2018/054849
§ 371 (c)(1),
(2) Date: Sep. 24, 2019

(87) PCT Pub. No.: WO2018/172024
PCT Pub. Date: Sep. 27, 2018

(65) Prior Publication Data
US 2020/0015767 A1    Jan. 16, 2020

(30) Foreign Application Priority Data
Mar. 24, 2017   (EP) .................... 17162697

(51) Int. Cl.
*A61B 6/00* (2006.01)
*A61B 6/08* (2006.01)

(52) U.S. Cl.
CPC ............ *A61B 6/484* (2013.01); *A61B 6/08* (2013.01); *A61B 6/4291* (2013.01); *A61B 6/589* (2013.01)

(58) Field of Classification Search
CPC ......... A61B 6/484; A61B 6/08; A61B 6/4291; A61B 6/589
See application file for complete search history.

(56) References Cited

U.S. PATENT DOCUMENTS

| | | | |
|---|---|---|---|
| 5,446,780 A | 8/1995 | Aichinger | |
| 6,934,409 B2 * | 8/2005 | Ohara | A61B 6/4233 250/370.09 |

(Continued)

FOREIGN PATENT DOCUMENTS

JP    4042287 A    9/2011

OTHER PUBLICATIONS

PCT International Search Report, International application No. PCT/EP2018/054849, dated Jun. 11, 2018.

(Continued)

*Primary Examiner* — Courtney D Thomas
(74) *Attorney, Agent, or Firm* — Larry Liberchuk

(57) ABSTRACT

The present invention relates to grating based Dark-Field and/or phase-contrast X-ray imaging. In order to improve the quality of an image, a radiography system (10) for grating based Dark-Field and/or phase-contrast X-ray imaging for imaging a patient by irradiating the patient is provided. The system comprises a source unit (12), a detection unit (14) and a patient support unit (16) with a patient abutting surface (18). The source unit (12) and the detection unit (14) are arranged along an optical axis (13) and the patient support unit (16) is arranged in between. Further, an abutting distance ($d_A$) between the source unit (12) and the patient abutting surface (18) along the optical axis (13) is adaptable. The abutting distance ($d_A$) and an actual sensitivity, based on the abutting distance ($d_A$), are taken into (Continued)

account for imaging, such that a trade-off between sensitivity and field of view in a patient specific manner is achievable, e.g. the best trade-off.

13 Claims, 3 Drawing Sheets

(56) References Cited

U.S. PATENT DOCUMENTS

| | | |
|---|---|---|
| 2004/0145671 A1 | 7/2004 | Wang |
| 2009/0272907 A1 | 11/2009 | Hara |
| 2010/0080436 A1* | 4/2010 | Ohara .................. A61B 6/4291 382/132 |
| 2010/0254512 A1* | 10/2010 | Takeda .................. A61B 6/588 378/62 |
| 2012/0087470 A1 | 4/2012 | Omote |
| 2013/0108015 A1 | 5/2013 | Kottler |
| 2014/0037059 A1 | 2/2014 | Suft |

OTHER PUBLICATIONS

Tilman Donath et al., "Inverse Geometry for Grating-Based X-Ray Phase-Contrast Imaging", Journal of Applied Physics, vol. 106, No. 5, Sep. 11, 2009 (Sep. 11, 2009), pp. 1-7, XP055363341.

* cited by examiner

SENSITIVITY OPTIMIZED PATIENT POSITIONING SYSTEM FOR DARK-FIELD X-RAY IMAGING

FIELD OF THE INVENTION

The present invention relates to a radiography system for grating based Dark-Field and/or phase-contrast X-ray imaging and a method for capturing a Dark-Field and/or phase-contrast X-ray image.

BACKGROUND OF THE INVENTION

Standard X-ray imaging techniques rely on a decrease of the X-ray beam's intensity due to attenuation by an object when traversing the object to be irradiated, which can be measured with the assistance of an X-ray detector. By using interferometric methods, for instance by using a Talbot-Lau type interferometer with three gratings in the beam, two additional physical effects create contrast that can be used for imaging. Phase-contrast X-ray imaging uses information concerning changes in the phase by refraction of an X-ray beam that passes through an object in order to create image data. Dark-Field contrast X-ray imaging uses information concerning small-angle scattering. Dark-Field and/or phase-contrast X-ray imaging may take place utilizing inverse geometry. However, it has been shown that there is a trade-off between the sensitivity of the system and the field of view that is achieved.

SUMMARY OF THE INVENTION

There may be a need to improve the quality of an image captured with a radiography system for grating based Dark Field X-ray phase contrast imaging.

The object of the present invention is solved by the subject-matter of the independent claims, wherein further embodiments are incorporated in the dependent claims. It should be noted that the following described aspects of the invention apply also for the radiography system for grating based Dark-Field and/or phase-contrast X-ray imaging, and for a method for capturing a Dark-Field and/or phase-contrast X-ray image.

According to the present invention, a radiography system for grating based Dark-Field and/or phase-contrast X-ray imaging is provided. The radiography system for grating based Dark-Field and/or phase-contrast X-ray imaging comprises a source unit, a detection unit and a patient support with a patient abutting surface. The source unit and the detection unit are arranged along an optical axis and the patient support is arranged in between. The distance between the source unit and the patient abutting surface along the optical axis is adaptable. The abutting distance and an actual sensitivity, based on the abutting distance, are taken into account for imaging, such that a trade-off between sensitivity and field of view in a patient specific manner can be achieved.

As an effect, a high sensitivity to small angle scattering inside the object to be irradiated, i.e. the patient, is avoided, since the patient can be positioned in an adapted way. Positioning closer to the source unit of the radiation increases the magnification and thus decreases the field of view. A high sensitivity is provided as it results in a better contrast-to-noise-ratio which typically facilitates the diagnosis. Thus, the image quality is improved.

In another example, a radiography system for grating based Dark-Field and/or phase-contrast X-ray imaging is provided. The radiography system for grating based Dark-Field and/or phase-contrast X-ray imaging comprises a source unit, a detection unit and a patient support with a patient abutting surface. The source unit and the detection unit are arranged along an optical axis and the patient support is arranged in between. The distance between the source unit and the patient abutting surface along the optical axis is adaptable.

The distance between the source unit and the patient abutting surface can also be referred to as abutting distance $d_A$.

The technology of grating based Dark-Field and/or phase-contrast X-ray imaging requires an insertion of three gratings into the beam, or at least two when the source provides coherent X-rays.

In an example, the source unit comprises a first grating G0 and a second grating G1, provided downstream the first grating, and the detection unit comprises a third grating G2. The maximum sensitivity is reached when the patient is positioned at G1 and decreases linear to 0 at G2.

The movability of the patient support unit relates to a relocating of the patient support unit. The relocating can also be referred to as shifting.

According to an example, the source unit comprises a first grating G0 and a second grating G1 and the detection unit comprises a third grating G2; the radiography system for grating based Dark-Field and/or phase-contrast X-ray imaging utilizes inverse geometry where the distance between the first grating G0 and the second grating G1 is smaller than the distance between the second grating G1 and the third grating G2.

The term inverse geometry relates to a configuration, where the distance between G0 and G1 is smaller than the distance between G1 and G2 and where the object, i.e. the patient, is placed between the second and the third grating.

According to an example, the radiography system for grating based Dark-Field and/or phase-contrast X-ray imaging utilizes symmetric geometry, where the distance between G0 and G1 is the same as the distance between G1 and G2.

In another, alternative option, the radiography system for grating based Dark-Field and/or phase-contrast X-ray imaging utilizes so-called direct geometry, where the distance between G0 and G1 is larger than the distance between G1 and G2. For example, the patient is placed between the first and the second grating.

In an example, the abutting distance $d_A$ between the source unit and the patient abutting surface along the optical axis is adaptable by moving the source unit.

The contact surface for the patient may have several discrete positions along the optical axis, e.g., large, medium, and small patient.

According to another example, the radiography system for grating based Dark-Field and/or phase-contrast X-ray imaging comprises a position detection device and an image generation unit. The position detection device is configured to determine an actual position of the patient abutting surface and to feed the actual position into the image generation unit, and the image generation unit uses an actual position to generate an image.

The generation of data for an image takes the actual sensitivity into account to generate an image. The patient support is provided between the source unit and the detection unit along the optical axis such that the best trade-off between sensitivity and field of view in a patient specific manner is achieved.

According to an example, the radiography system for grating based Dark-Field and/or phase-contrast X-ray imaging comprises an indicating unit for indicating a field of view.

According to another example, the position detection device is configured to determine the abutting distance $d_A$ between the source unit and the patient abutting surface.

According to an example, the position detection device comprises a stereo camera. The stereo camera is configured to determine an abutting distance $d_A$ between the source unit and the patient abutting surface.

It is proposed to use this basic technology to calculate and set the most appropriate (i.e. largest) sensitivity that would still allow to image the entire object to be irradiated. The stereo camera is configured to determine the size of the patient and determines an appropriate abutting distance $d_A$ between the source and the patient abutting surface.

According to another example, the radiography system for grating based Dark-Field and/or phase-contrast X-ray imaging is configured to determine a geometric shape of the patient to be irradiated. The system is also configured to determine the field of view based on the geometric shape and to determine based on the field of view the distance between the source unit and the patient abutting surface, i.e. the object to be irradiated. The distance between the source unit and the patient abutting surface can also be referred to as patient distance $d_P$, or object distance $d_O$.

In an example, the stereo camera is used together with an anatomical model of a human thorax to estimate the distance of the mid-lung plane to the contact surface.

According to another example, the system supports at least two acquisition modes, one with large field of view and low dark-field sensitivity (bottom surface close to the detector) and one with small field of view and high dark-field sensitivity (surface farther away from the detector).

According to the invention, also a method for capturing a Dark-Field and/or phase-contrast X-ray image, by using the radiography system according to one of the preceding examples, is provided. The method comprises the following steps:

a) adapting an abutting distance $d_A$ between the patient abutting surface and the source unit along an optical axis;
b) temporary fixing the patient abutting surface in a first position;
c) irradiating the patient to be irradiated; and
d) capturing the Dark-Field and/or phase-contrast X-ray image.

According to an example, the step a) of adapting of the abutting distance $d_A$ between the patient abutting surface and the source unit along the optical axis comprises the following sub-steps:

a1) positioning a patient to be irradiated between a source unit and a patient abutting surface;
a2) determining an actual position between the source unit and the patient abutting surface until a field of view corresponds to an area of interest, wherein the target distance $d_T$ is used to adapt the abutting distance;
a3) Feeding the actual position between the source unit and the patient abutting surface to an image generation unit, wherein the image generation unit is adapted to take an actual sensitivity, based on the actual position between the source unit and the patient to be irradiated, into account to generate an image.

According to the invention, a computer program element is provided for controlling a radiography system for grating based Dark-Field and/or phase-contrast X-ray imaging, which, when being executed by a processing unit, is adapted to perform the method steps for capturing a Dark-Field and/or phase-contrast X-ray image.

The invention relates a system and a method to locate patient along an optical axis for grating based Dark Field and/or phase-contrast X-ray imaging. The patient is located either next to a source unit or a detection unit. An indicating unit illuminates with its cone of light the field of view. In the next step the patient is moved until the field of view corresponds with the area of interest. The distance $d_T$ between the source unit and the patient is taken into account to generate an image with the optimal trade-off between the sensitivity of the system and the field of view.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the following drawings.

DETAILED DESCRIPTION OF EMBODIMENTS

Figure 1:
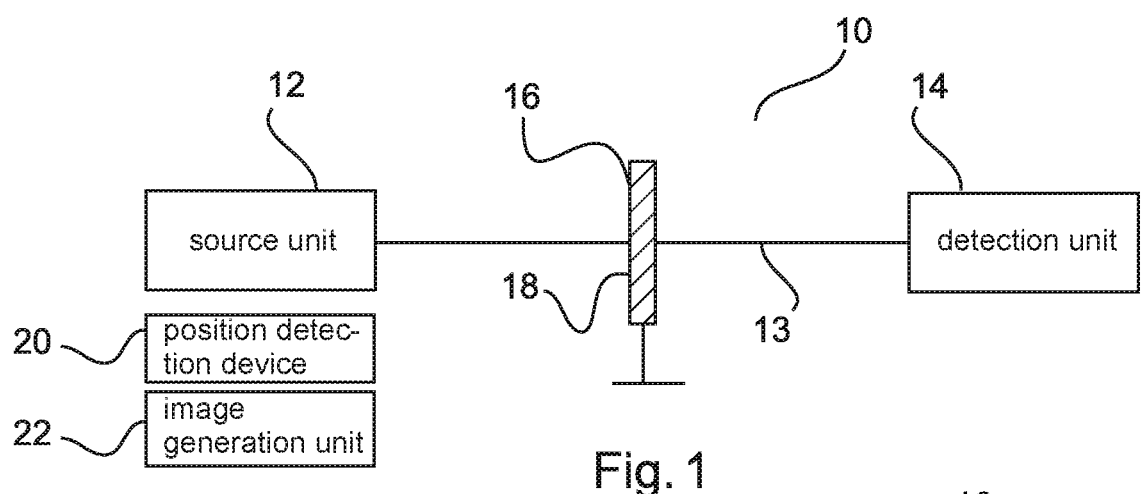
FIG. 1 shows a schematic view of a radiography system for grating based Dark-Field and/or phase-contrast X-ray imaging.

FIG. 1 shows a radiography system 10 for grating based Dark-Field and/or phase-contrast X-ray imaging. The radiography system 10 for grating based Dark-Field and/or phase-contrast X-ray imaging comprises a source unit 12, a detection unit 14 with a patient abutting surface 18. The source unit 12 and the detection unit 14 are arranged along an optical axis 13 and the patient support unit 16 with the patient abutting surface 18 is arranged in between. The patient support unit is movably arranged to be temporarily fixed in at least two different positions along the optical axis 13. The radiography system 10 for grating based Dark-Field and/or phase-contrast X-ray imaging may further comprise a position detection device 20 and an image generation unit 22. The position detection device 20 is configured to determine an actual position of the patient abutting surface 18 and to feed the actual position into the image generation unit 22, and the image generation unit 22 uses an actual position to generate an image.

Figure 2A:
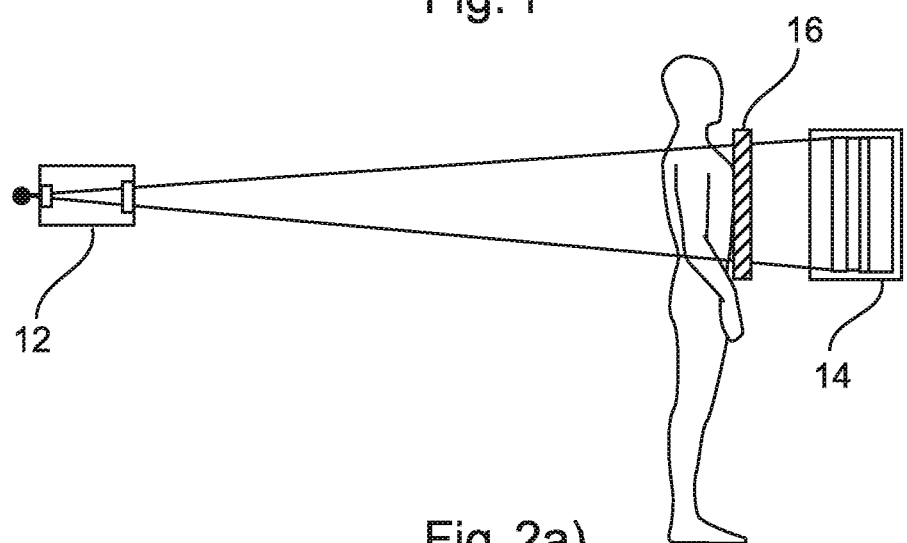
FIG. 2 shows a schematic view of a patient arranged in radiography system in two different positions.
Figure 2B:
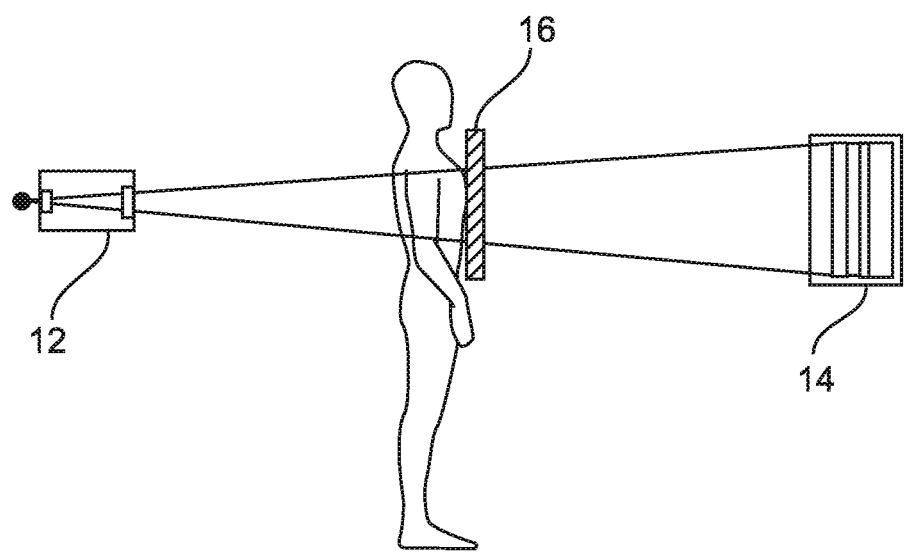

FIG. 2a and FIG. 2b show two different positions of a patient standing next to the patient abutting surface 18. In FIG. 2a, the distance between the patient to the detection unit 14 is smaller compared to the field of view 26 in FIG. 2b, and therefore the field of view 26 is increased.

According to an example, the abutting distance $d_A$ between the source unit 12 and the patient abutting surface 18 along the optical axis 13 is adaptable in a discrete manner.

In an example, the abutting distance $d_A$ between the source unit 12 and the patient abutting surface 18 along the optical axis 13 is separated in several discrete positions along the optical axis 13, e.g., large, medium, and small patient.

In an example, the discrete positions comprise steps of 1 cm. In another example the discrete positions comprise steps of 1 cm to 5 cm.

According to another example, the abutting distance $d_A$ between the source unit 12 and the patient abutting surface 18 along the optical axis 13 is adaptable in a continuous manner.

According to an example, the patient abutting surface 18 for the patient is moved continuously along the optical axis 13 between a minimum and maximum position.

Figure 3:
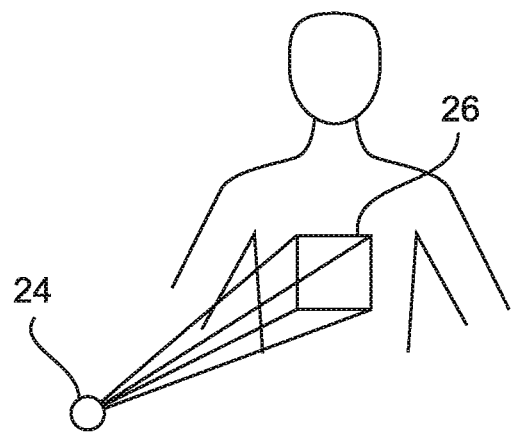
FIG. 3 shows a schematic view of a field of view of a region of interest.

FIG. 3 shows a field of view 26 of a chest of a patient. The field of view 26 is indicated via an indicating unit 24. The indicating unit 24 may be configured as a light visor. The light visor indicates the borders of the area to be irradiated by X-ray. With its cone of light, the light visor illuminates the field of view.

The term field of view can also be referred as area to be inspected.

In an example, the indicating unit is a focal layer positioning beam.

The area to be inspected can also be referred to as an area of interest.

The sensitivity S of the system and a field of view of image have an interdependency in accordance with the distance $d_A$ of the source unit 12 to the patient abutting surface 18.

Figure 4A:
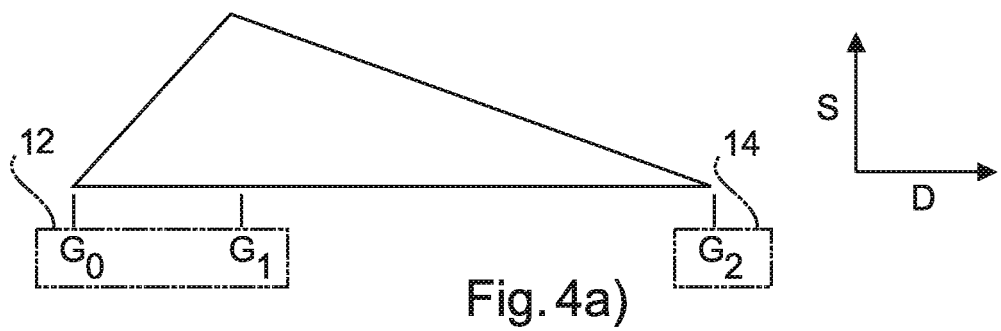
FIGS. 4a, 4b and 4c show the distributions of the sensitivity and the field of view along the optical axis.

FIG. 4a shows the distribution of the sensitivity S along the optical axis 13 starting from grating G0 with a sensitivity S of 0 (zero) rising on a linear basis to a maximum sensitivity at the grating G1. From the grating G1, the sensitivity S decreases on a linear basis to 0 at the grating G2. According to an example, the grating G0 and the grating G1 are united in the source unit 12.

Figure 4B:
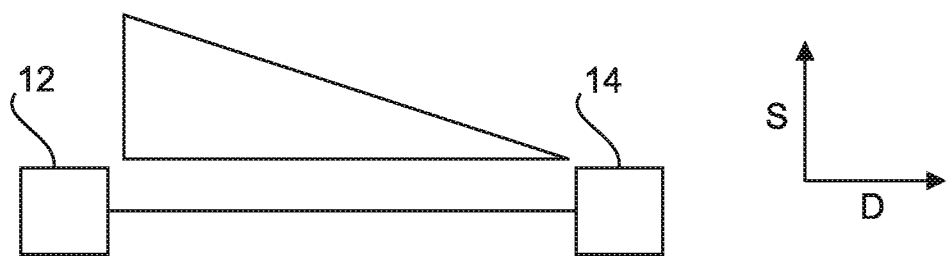

FIG. 4b shows the distribution of the sensitivity S along the optical axis D. The sensitivity S has its maximum at the radiation outlet of the source unit 12, e.g. the X-ray window of the tube, and decreases on a linear basis to 0 at the grating G2 arranged in the detection unit 14.

Figure 4C:
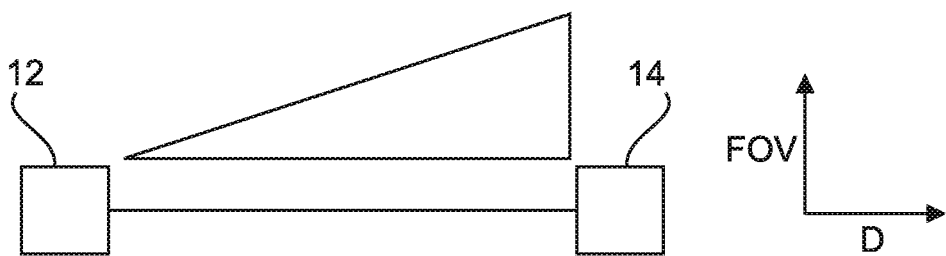

FIG. 4c shows the distribution of the field of view 26 along the optical axis D. The minimum field of view 26 is just next to the source unit 12 and rises on a linear basis to a maximum just next to the detection unit 14.

In an example, not further shown in detail, the system supports at least two acquisition modes, one with large field of view and low dark-field sensitivity (bottom surface close to the detector) and one with small field of view and high dark-field sensitivity (surface farther away from the detector).

Figure 5:
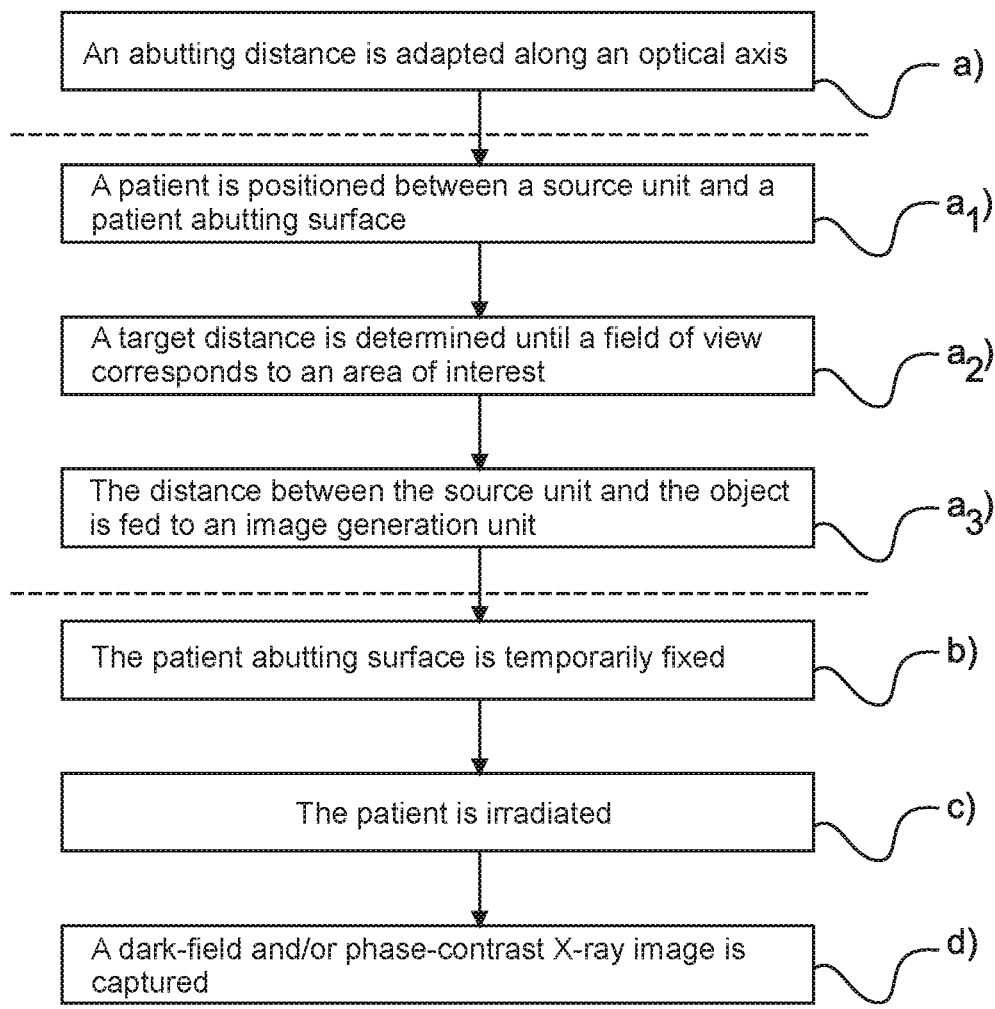
FIG. 5 shows an example of a method for capturing a Dark-Field and/or phase-contrast X-ray image.

FIG. 5 shows a method 100 for capturing a Dark-Field and/or phase-contrast X-ray image comprising the following steps:

In a first step 102, also referred to as step a), an abutting distance $d_A$ between the patient abutting surface and the source unit is adapted along an optical axis.

In a second step 104, also referred to as step b), the patient abutting surface is temporary fixed.

In a third step 106, also referred to as step c), the patient to be irradiated is irradiated.

In a fourth step 108, also referred to as step d), a Dark-Field and/or phase-contrast X-ray image is captured.

In an option, the method is expanded with three substeps for step a):

In a first substep 110, also referred to as step a1), a patient to be irradiated is positioned between a source unit and a patient abutting surface.

In a second substep 112, also referred to as step a2), a target distance $d_T$ between the source unit and the object to be irradiated is determined until a field of view corresponds to an area of interest, wherein the target distance $d_T$ is used to adapt the distance.

In a third substep 114, also referred to as step a3), the distance between the source unit and the object to be irradiated is feeded to an image generation unit, wherein the image generation unit is adapted to take an actual sensitivity S, based on the distance between the source unit and the object to be irradiated, into account to generate an image.

In an example, the positioning takes place in a discrete manner or a continuous manner wherein the adapting of distance is carried out via a stereo camera.

According to an example, the distance between the patient abutting surface and the source unit is adapted until a field of view corresponds to an area of interest.

The term "corresponds" can also be referred to as a maximum proportion of area of interest in the field of view.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A radiography system for grating based dark-field and/or phase-contrast X-ray imaging for imaging a patient by irradiating the patient, the system comprising:
   an X-ray source and an X-ray detector that are arranged along an optical axis;
   a patient supporter including a patient abutting surface,
      wherein the patient supporter is arranged between the X-ray source and the X-ray detector, and
      wherein an abutting distance between the X-ray source and the patient abutting surface along the optical axis is adaptable; and
   processor circuitry configured to execute instructions to:
      determine an actual sensitivity of the radiography system, based on the abutting distance; and
      generate an image of the patient based on the determined actual sensitivity of the radiography system.

2. The radiography system according to claim 1,
   wherein the X-ray source comprises a first grating and a second grating, and the X-ray detector comprises a third grating; and
   wherein a distance between the first grating and the second grating is smaller than a distance between the second grating and the third grating.

3. The radiography system according to claim 1, wherein the abutting distance between the X-ray source and the patient abutting surface along the optical axis is adaptable by moving the patient support.

4. The radiography system according to claim 1, wherein the abutting distance between the X-ray source and the patient abutting surface along the optical axis is adaptable in a discrete manner.

5. The radiography system according to claim 1, wherein the abutting distance between the X-ray source and the patient abutting surface along the optical axis is adaptable in a continuous manner.

6. The radiography system according to claim 1,
   wherein the processor circuitry is further configured to determine an actual position of the patient abutting surface; and
   wherein the generating of the image of the patient is based on the actual position of the patient abutting surface.

7. The radiography system according to claim 6, wherein the processor circuitry is further configured to indicate a field of view.

8. The radiography system according to claim 6,
   further comprising a stereo camera, and
      wherein the processor circuitry is further configured to determine the abutting distance between the X-ray source and the patient abutting surface based on a capture of the stereo camera.

9. The radiography system according to claim 1, wherein the processor circuitry is further configured to:
   determine a geometric shape of the patient to be irradiated;
   determine a field of view based on the geometric shape; and
   determine, based on the field of view, the abutting distance between the X-ray source and the patient abutting surface.

10. The radiography system according to claim 1, wherein the system supports at least first and second acquisition modes,
    wherein the first acquisition mode includes a first field of view and a first dark-field sensitivity, and
    wherein the second acquisition mode includes a second field of view that is smaller than the first field of view and a second dark-field sensitivity that is higher than the first dark-field sensitivity.

11. A method for capturing a dark-field and/or phase-contrast X-ray image, the method comprising:
    adapting an abutting distance between a patient abutting surface and an X-ray source along an optical axis;
    temporarily fixing the patient abutting surface;
    irradiating a patient that abuts on the patient abutting surface;
    determining an actual sensitivity of a radiography system, based on the abutting distance; and
    generating an image of the patient based on the determined actual sensitivity of the radiography system.

12. The method according to claim 11, further comprising:
    positioning the patient to be irradiated between the X-ray source and the patient abutting surface; and
    determining a target distance between the X-ray source and the patient to be irradiated until a field of view corresponds to an area of interest, wherein the target distance is used to adapt the abutting distance.

13. A non-transitory computer-readable medium having one or more executable instructions stored thereon, which, when executed by at least one processor, cause the at least one processor to perform a method for capturing a dark-field and/or phase-contrast X-ray image, the method comprising:
    adapting an abutting distance between a patient abutting surface and an X-ray source along an optical axis;
    temporarily fixing the patient abutting surface;
    irradiating a patient that abuts on the patient abutting surface;
    determining an actual sensitivity of a radiography system, based on the abutting distance; and
    generating an image of the patient based on the determined actual sensitivity of the radiography system.

* * * * *